United States Patent
Omidbakhsh

(10) Patent No.: US 11,712,321 B2
(45) Date of Patent: Aug. 1, 2023

(54) APPARATUS AND METHOD FOR ADJUSTING A VOLUME OF A BASIN OF A TREATMENT APPARATUS

(71) Applicant: ASP Global Manufacturing GmbH, Schaffhausen (CH)

(72) Inventor: Navid Omidbakhsh, Irvine, CA (US)

(73) Assignee: ASP Global Manufacturing GMBH

( * ) Notice: Subject to any disclaimer, the term of this patent is extended or adjusted under 35 U.S.C. 154(b) by 516 days.

(21) Appl. No.: 16/655,649

(22) Filed: Oct. 17, 2019

(65) Prior Publication Data
US 2020/0155267 A1 May 21, 2020

Related U.S. Application Data

(60) Provisional application No. 62/767,775, filed on Nov. 15, 2018.

(51) Int. Cl.
*A61B 90/70* (2016.01)
*A61B 1/12* (2006.01)
*A61L 2/18* (2006.01)

(52) U.S. Cl.
CPC .............. *A61B 90/70* (2016.02); *A61B 1/123* (2013.01); *A61B 2090/701* (2016.02)

(58) Field of Classification Search
CPC ............ A61B 90/70; A61B 1/123; A61L 2/18
USPC ........................................................ 422/294
See application file for complete search history.

(56) References Cited

U.S. PATENT DOCUMENTS

| | | | | |
|---|---|---|---|---|
| 6,589,481 B1 * | 7/2003 | Lin | ........................... | A61L 2/16 422/305 |
| 2001/0036422 A1 * | 11/2001 | Lin | ......................... | A61L 2/208 422/294 |
| 2003/0082069 A1 * | 5/2003 | Kuzyk | ................. | A01N 1/0284 422/1 |
| 2009/0060798 A1 * | 3/2009 | Williams | ................... | A61L 2/18 422/111 |
| 2015/0010432 A1 * | 1/2015 | Olson | ...................... | A61L 2/208 422/292 |

FOREIGN PATENT DOCUMENTS

| | | |
|---|---|---|
| EP | 0923949 A2 | 6/1999 |
| EP | 2572628 A1 | 3/2013 |
| EP | 3440986 A1 | 2/2019 |
| WO | 2012148589 A2 | 11/2012 |

OTHER PUBLICATIONS

International Search Report and Written Opinion for International Patent Application No. PCT/IB2019/059186, dated Feb. 20, 2020.

* cited by examiner

*Primary Examiner* — Kevin Joyner
(74) *Attorney, Agent, or Firm* — Lerner David LLP

(57) ABSTRACT

An apparatus and a method for adjusting a void volume of a basin of a treatment apparatus are provided. A treatment apparatus comprising a basin and an expandable member are provided. The expandable member may be disposed in the basin. The expandable member may be configured to expand from a first state to a second state to adjust the void volume of the basin. A void volume of the basin when the expandable member is in the second state is less than the void volume of the basin when the expandable member is in the first state.

11 Claims, 3 Drawing Sheets

APPARATUS AND METHOD FOR ADJUSTING A VOLUME OF A BASIN OF A TREATMENT APPARATUS

CROSS REFERENCE TO RELATED APPLICATIONS

The present application claims priority under 35 U.S.C. § 120 to U.S. provisional Patent Application Ser. No. 62/767,775, filed Nov. 15, 2018, which is incorporated by reference herein in its entirety.

FIELD

The present disclosure relates to an apparatus and method for adjusting a void volume of a basin of a treatment apparatus.

BACKGROUND

Medical devices are used in numerous procedures in the medical field. These devices are as varied as the treatments themselves. As such, proper care of these devices is critical for efficient and effective application and the proper corresponding treatment of the patient.

After a medical device, such as an endoscope, is used in a medical procedure, the device is treated by one or more of cleaning, disinfecting, and sterilizing in order to prepare the device for its next use. The treatment may include placing the medical device in a re-processing machine and treating the device with a treatment agent. After the treatment process is completed, the medical device is ready for another use. While the medical device is non-sterile, non-disinfected and/or waiting to be cleaned, disinfected, and/or sterilized, the device is typically unavailable for use, resulting in downtime of the medical device.

SUMMARY

In one example, the present disclosure provides a treatment apparatus comprising a basin and an expandable member. The expandable member is disposed in the basin and is configured to expand from a first state to a second state. A void volume of the basin when the expandable member is in the second state is less than the void volume of the basin when the expandable member is in the first state.

In another example, the present disclosure provides a treatment apparatus comprising a basin and an expandable member. The expandable member has a cavity therein and is disposed in the basin. The expandable member is configured to expand from a first state to a second state responsive to an expansive pressure within the cavity. A void volume of the basin when the expandable member is in the second state is less than the void volume of the basin when the expandable member is in the first state.

In yet another example, the present disclosure provides a method of adjusting a void volume in a basin of a treatment apparatus. A device is introduced into the basin of the treatment apparatus. The basin comprises a void volume suitable to receive the device and a treatment agent. The void volume is adjusted to an adjusted void volume by at least one of expanding and contracting an expandable member positioned in the basin.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Figure 1:
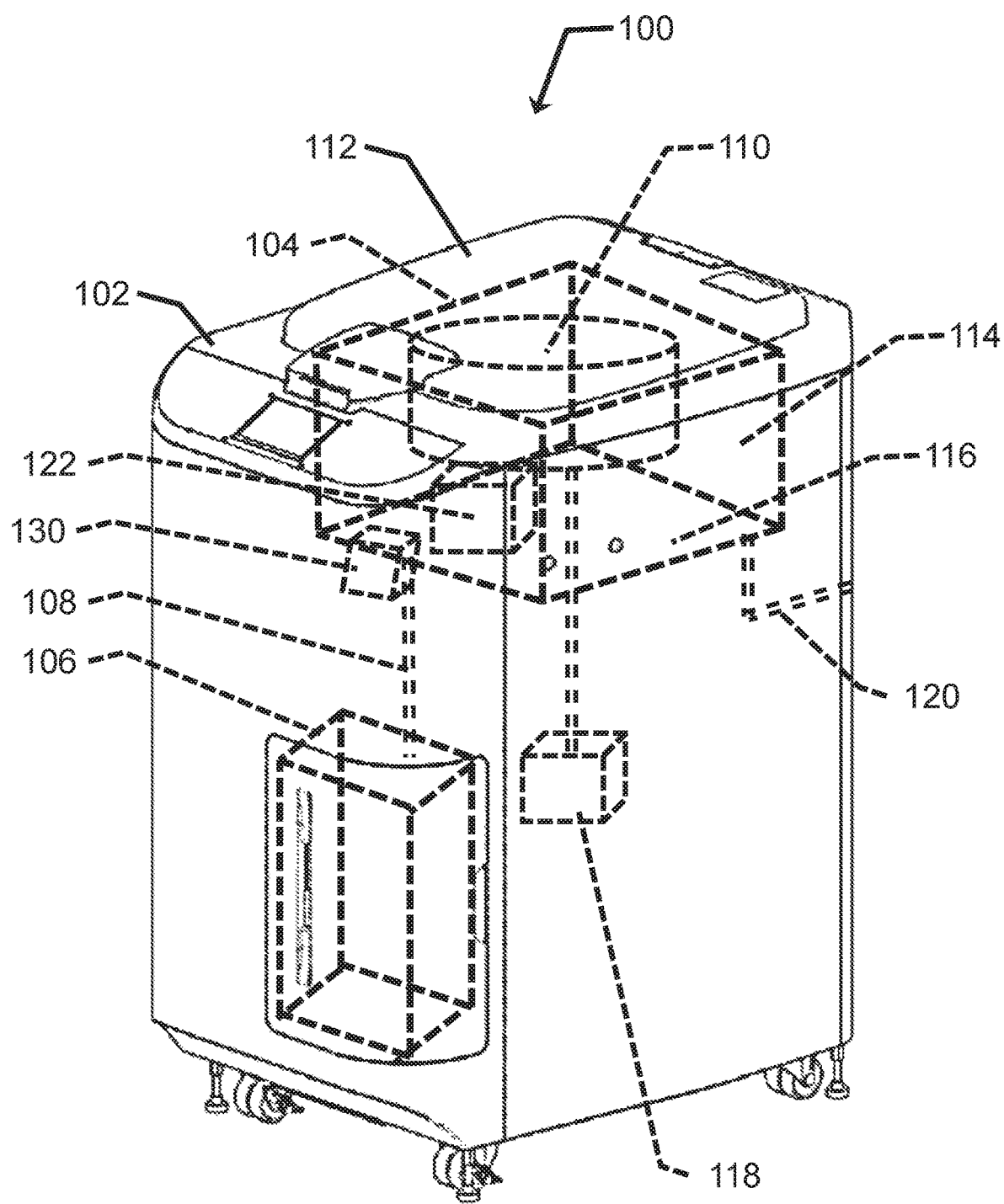
FIG. 1 is a perspective view of a treatment apparatus comprising an expandable member according to the present disclosure.

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting, exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

Any references herein to "various examples," "some examples," "one example," "an example," similar references to "aspects," or the like, means that a particular feature, structure, or characteristic described in connection with the example is included in at least one example. Thus, appearances of the phrases "in various examples," "in some examples," "in one example," "in an example," similar references to "aspects," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited.

The grammatical articles "a," "an," and "the," as used herein, are intended to include "at least one" or "one or more," unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

A device can undergo a treatment process to prevent cross-contamination and the spread of disease. As used herein, a "treatment process" may be a cleaning process, a disinfecting process, a sterilization process, the like, and combinations thereof. A treatment process may be either manual, automated, or some combination thereof, and may utilize a treatment agent. As used herein, a "treatment agent" can comprise at least one of a cleaning agent, a disinfectant, and a sterilant. As used herein a "cleaning process" means a treatment process employing a cleaning agent that removes and/or eliminates debris such as, for example, a dirt, a dust, a particle, an oil, a protein, a carbohydrate, and the like. As used herein, a "cleaning agent" means a type of treatment agent that removes and/or eliminates debris during a cleaning process such as, for example, a surfactant and/or a detergent.

A disinfecting process and a sterilization process can remove and/or eliminate a bioburden from a device. A bioburden may be, for example, a bacterium (e.g., *mycobacterium*, bacterial spores), an archaeon, a eukaryote, a virus, a fungus, and/or other forms of biological agents. Bacterial spores (e.g., endospores) are a form of bacteria which are dormant and highly resistive to physical and chemical degradation. As used herein, a "disinfecting process" means a treatment process that substantially removes a bioburden except for bacterial spores. As used herein, "substantially remove" means that at least 99% of the bioburden has been removed from the device such as, for example, at least 99.9% of the bioburden, at least 99.99% of the bioburden, at least 99.999% of the bioburden, or at least 99.9999% of the bioburden has been removed from the device. As used herein, a "sterilization process" means a treatment process which substantially removes a bioburden including bacterial spores. The sterilization process may include, for example, the addition of heat, freezing, a sterilant, irradiation, pressure, and combinations thereof. The sterilant may comprise a chemical capable of sterilization. The disinfection process may include, for example, the addition of heat, a disinfectant, irradiation, pressure, and combinations thereof. The disinfectant may comprise a chemical capable of disinfection.

The present disclosure is directed to apparatus and methods for adjusting a void volume of a basin of a treatment apparatus for a device, such as a medical device (e.g., re-processor for an endoscope). Although it is contemplated that any treatment apparatus and medical device may suitably employ the apparatus and methods described herein, for the purpose of illustration and convenience, the present disclosure may place particular emphasis on a treatment apparatus in the form of a re-processor for an endoscope. Such emphasis, if any, is meant only to be illustrative and not meant to narrow or limit aspects of the present disclosure to particular treatment apparatus or medical devices, except where explicitly set forth in the claims.

A device, such as an endoscope, can be very expensive, and healthcare facilities typically do not have a budget sufficient to keep a large inventory of endoscopes on hand. Therefore, healthcare facilities typically treat the endoscopes between uses as quickly as possible. A treatment apparatus for a device can rinse, clean, disinfect, sterilize, and/or dry the device in many ways. The device can be manually pre-cleaned before being placed in the treatment apparatus, or the treatment apparatus may perform the cleaning process. The steps of the treatment process may be selected based on the device type, the treatment apparatus type, and the level of soil of the device. For example, if the treatment apparatus is used mainly to disinfect the device, an initial water rinse, a cleaning process, and/or a subsequent water rinse may be omitted. If the treatment apparatus is used mainly to clean the device, the disinfecting process and/or sterilizing process can be omitted.

A basin of a treatment apparatus should be sized to accommodate the various ranges of sizes that a device may have. For example, if the device is an endoscope, the basin of the apparatus may have a volume large enough to receive a large endoscope, but this design can result in inefficient use of volume inside the basin when treating a small endoscope. For example, where the treatment apparatus is an endoscope re-processor, an endoscope may be positioned within the basin and immersed in a treatment agent (e.g., liquid cleaner, liquid disinfect, liquid sterilant). In some cases the treatment agent is heated. The time to fill the basin and/or heat the liquid typically increases the length of a treatment process. In addition, the volume of the void in the basin may vary depending on the number and size of the devices to be treated. Following placement of the device(s), treatment agent is typically needed to fill the remaining void in the basin which can immerse the instrument to be decontaminated within the treatment agent. At times of low volume utilization in the basin of a treatment apparatus (e.g., high void volume), excess treatment agent and/or excess energy to heat the treatment agent may be needed to fill the remaining void.

Thus, an apparatus and method of use thereof for adjusting a void volume of a basin of a treatment apparatus is provided. An expandable member can be disposed in the basin of the treatment apparatus to adjust the void volume, which can reduce the amount of treatment agent needed to fill the basin. The reduction in treatment agent can reduce filling time and heating time, which can reduce the length of a treatment process and downtime of the endoscope.

FIG. 1 illustrates a treatment apparatus 100 according to the present disclosure. As illustrated, the apparatus 100 can comprise a chamber 102 including a basin 104 in fluid communication with a reservoir 106. The chamber 102 may be suitable to receive a device 122, and can be suitable to perform a treatment process on the device 122. In various examples, the chamber 102 can comprise at least one of a heater (e.g., heating element), a pump, a wash arm, a spray nozzle, a tube, and other features known to one of ordinary skill in the art. In various examples, the chamber 102 can be at least one of a cleaning chamber, a disinfection chamber, and a sterilization chamber. For example, the treatment chamber 102 can be a single chamber that performs at least one of cleaning, disinfection, and sterilization. In certain examples, the device 122 can comprise an endoscope. In various examples, the apparatus 100 can comprise an endoscope re-processor (e.g., an automated endoscope re-processor).

The reservoir 106 can be configured to receive a treatment agent and can store the treatment agent until the treatment agent can be output into the basin 104. For example, there can be a plurality of reservoirs configured to receive treatment agents and can output the treatment agents to the basin 104. The basin 104 can be in fluid communication with the reservoir 106 via a treatment line 108. In various examples, a water line can be in fluid communication with the basin 104. The water line can comprise a filter to capture particles and/or contaminants and a regulator to adjust the water pressure. The treatment line 108 can be configured to receive the treatment agent from the reservoir 106 and transport the treatment agent to the basin 104. For example, the treatment line 108 can include at least one of a tube, a valve, and a pump. The treatment line 108 can control the amount of treatment agent provided to the basin 104. For example, the treatment agent can be metered into the basin 104 by the treatment line 108 until a select amount of treatment agent has been provided to the basin 104. The treatment agent can be removed from the basin 104 through a drain line 120 in fluid communication with the basin 104.

In example s where the chamber 102 comprises a heater 130, the heater 130 can be configured to heat the treatment agent to a temperature in a range of 30 degrees Celsius (° C.) to 80° C. The heater 130 can heat the treatment agent at various locations within the chamber 102, such as in the basin 104. The heater 130 can be in fluid communication with the treatment line 108 and can heat the treatment agent in the treatment line 108 and/or reservoir 106 prior to introduction of the treatment agent to the basin 104.

The treatment agent can comprise at least one of a cleaning solution (e.g., liquid cleaner), a disinfectant solution (e.g., liquid disinfectant), and a sterilant solution (e.g., liquid sterilant). The disinfectant solution can comprise at least one of an alcohol, an aldehyde, a quaternary ammonium compound, and an oxidizer (e.g., hydrogen peroxide, peracetic acid). The disinfectant can comprise ortho-phthalaldehyde (OPA), such as CIDEX-OPA™ available from Advanced Sterilization Products, A Division of Ethicon, Inc., a Johnson & Johnson company located in Irvine, Calif. The disinfectant can be a concentrated solution that can be diluted inside the basin or a ready to use solution that may not need further dilution.

The basin 104 can be configured to receive the device 122, such as, for example, an endoscope. The basin 104 may be any size and volume suitable to receive the device 122 for treatment. In certain examples the basin 104 can comprise a void volume, v, suitable to receive the device 122 and sufficient treatment agent from the reservoir 106 via the treatment line 108. As used herein, the term "void volume" refers to the remaining space within the basin 104 that is not occupied by a structure of the basin 104, the expandable member 110, or other components of the apparatus 100, e.g., the open volume suitable to receive the device 122 and treatment agent. The void volume may be a volume in the basin 104 that is suitable to immerse the device 122 within a treatment agent. The basin 104 can be structured to contain the device 122 and the treatment agent such that a suitable treatment process can be performed on the device 122. For example, the basin 104 can be structured to contact the device 122 with treatment agent. The treatment process can comprise filling the void volume, v, with treatment agent and, optionally, heating the treatment agent. The treatment agent can be circulated within the basin 104 in order to facilitate the treatment process. The void volume, v, can be filled with water to rinse the device 122. The treatment process can comprise drying the device 122. For example, the drying can comprise contacting the device 122 with an alcohol and/or flowing gas over the device 122.

Figure 2:
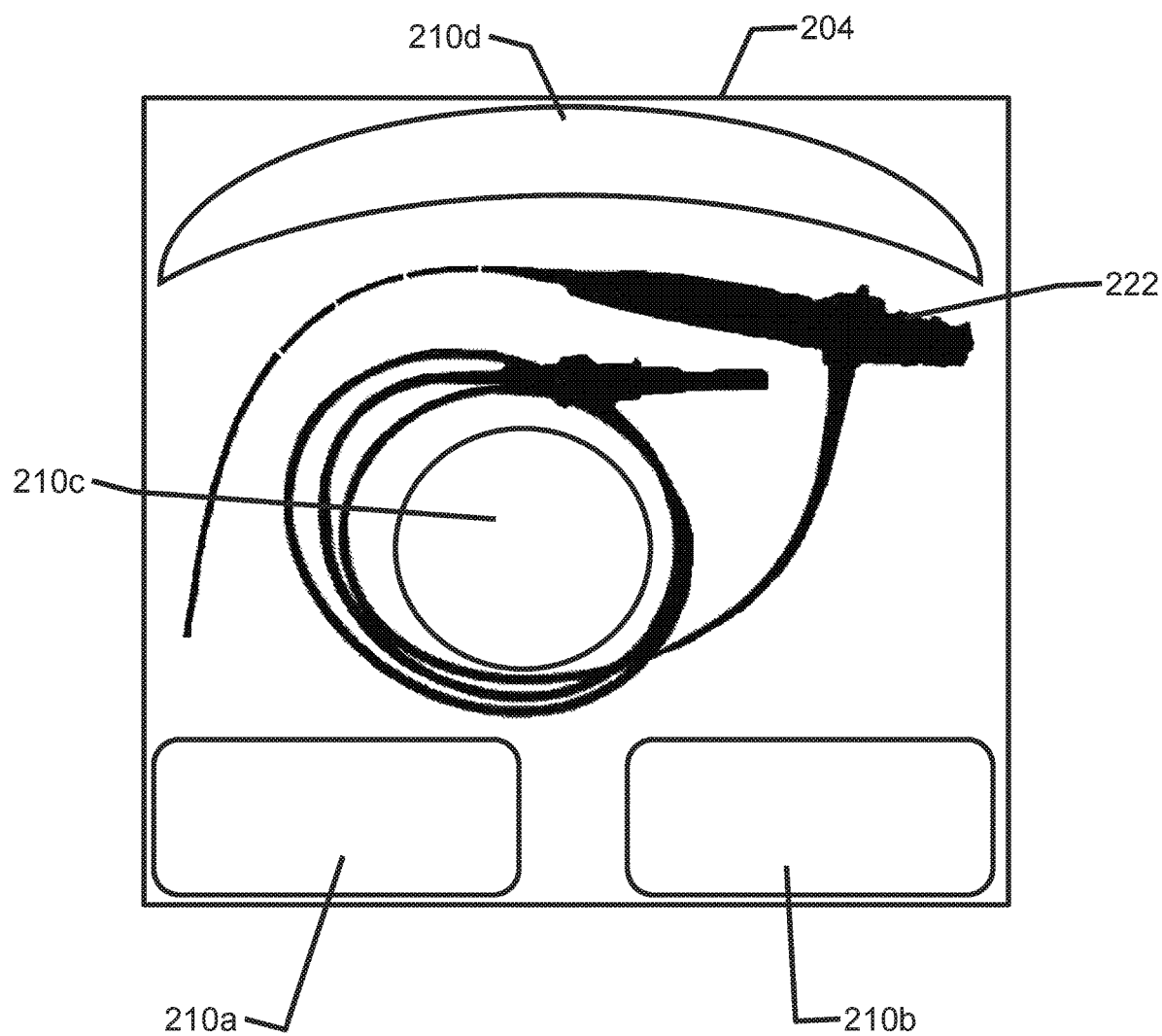
FIG. 2 is a schematic top-plan view of a basin comprising a plurality of expandable members according to the present disclosure.

As illustrated in FIGS. 1 and 2, an expandable member 110 can be disposed in the basin 104. The expandable member 110 can be operatively coupled to the basin 104. For example, the expandable member 110 can be operatively coupled to a basin cover 112, a side wall 114 of the basin 104, and/or a bottom 116 of the basin 104. It is contemplated that, one, two, or more expandable members may be disposed in the basin 104, as described in greater detail below.

The expandable member 110 can be expanded by various methods to alter the size of the volume of the basin 104, such as through inflation or mechanical movement. For example, the expandable member 110 can be configured to expand and/or contract to change the size (e.g., occupied volume) of the expandable member 110. For example, the expandable member 110 can expand from a first state to a second state. A first void volume, $v_1$, of the basin 104 when the expandable member 110 is in the first state can be less than a second void volume, $v_2$, of the basin 104 when the expandable member 110 is in the second state. Also expansion can be accomplished through movement of a mechanical member in communication with the expandable member 110 (e.g., a piston, an actuator), application of an electric current to the expandable member 110, and an increase in fluid pressure within the expandable member 110 (e.g., heat and/or adding/removing fluid). For example, the expandable member 110 can comprise an electroactive polymer, and application of and/or removal of electricity to/from the expandable member can change the expandable member 110 from a first state to a second state to alter size of the volume of the basin 104.

As illustrated, the expandable member can comprise a cavity and the expandable member 110 can expand from a first state to a second state responsive to an expansive pressure within the cavity of the expandable member 110. The expansive pressure can be up to a contractive pressure and can be suitable to provide a force to an inner surface of the expandable member 110 to increase the size of the expandable member 110. The contractive pressure can be suitable to lessen a force on the inner surface of the expandable member 110 to decrease the size of the expandable member 110. The expansive pressure required to increase the size of the expandable member 110 can be based on the composition of the expandable member 110 and the structure of the expandable member (e.g., wall thickness).

For example, the expansive pressure can be at least 0.1 pounds per square inch gauge (PSIG) such as, for example, at least 1 PSIG, at least 5 PSIG, at least 10 PSIG, at least 20 PSIG, at least 30 PSIG, or at least 40 PSIG. The expansive pressure can be up to 100 PSIG such as, for example, up to 40 PSIG, up to 30 PSIG, up to 20 PSIG, up to 10 PSIG, up to 5 PSIG, or up to 1 PSIG. The expansive pressure can be in a range of 0.1 PSIG to 100 PSIG, such as, for example, 5 PSIG to 30 PSIG or 1 PSIG to 40 PSIG. The contractive pressure can be at least 0.1 PSIG less than the expansive pressure, such as, for example, at least 1 PSIG less, at least 5 PSIG less, or at least 10 PSIG less than the expansive pressure.

The fluid pressure within the cavity of the expandable member 110 can be generated by movement of fluid into and/or out of the cavity of the expandable member 110. For example, the cavity of the expandable member 110 can be in fluid communication with a fluid source 118. The fluid source 118 can be suitable to control a fluid pressure in the cavity of the expandable member 110. In various examples, the fluid source 118 can comprise at least one of a gas source and a liquid source. The fluid source 118 can comprise at least one of a pump and a compressed gas cylinder. The pump can be suitable to provide a fluid to the cavity to increase the fluid pressure in the cavity (e.g., expand the expandable member 110) and/or remove fluid from the cavity to decrease the fluid pressure in the cavity (e.g., contract the expandable member 110). The compressed gas cylinder can be suitable to provide a gas (e.g., air) to the cavity to increase the fluid pressure and the gas can be released from the cavity by a vent (not shown in FIG. 1). It is contemplated that the fluid pressure within the cavity of the expandable member 110 can be generated by heating the expandable member 110 and/or fluid within the expandable member 110.

Figure 3:
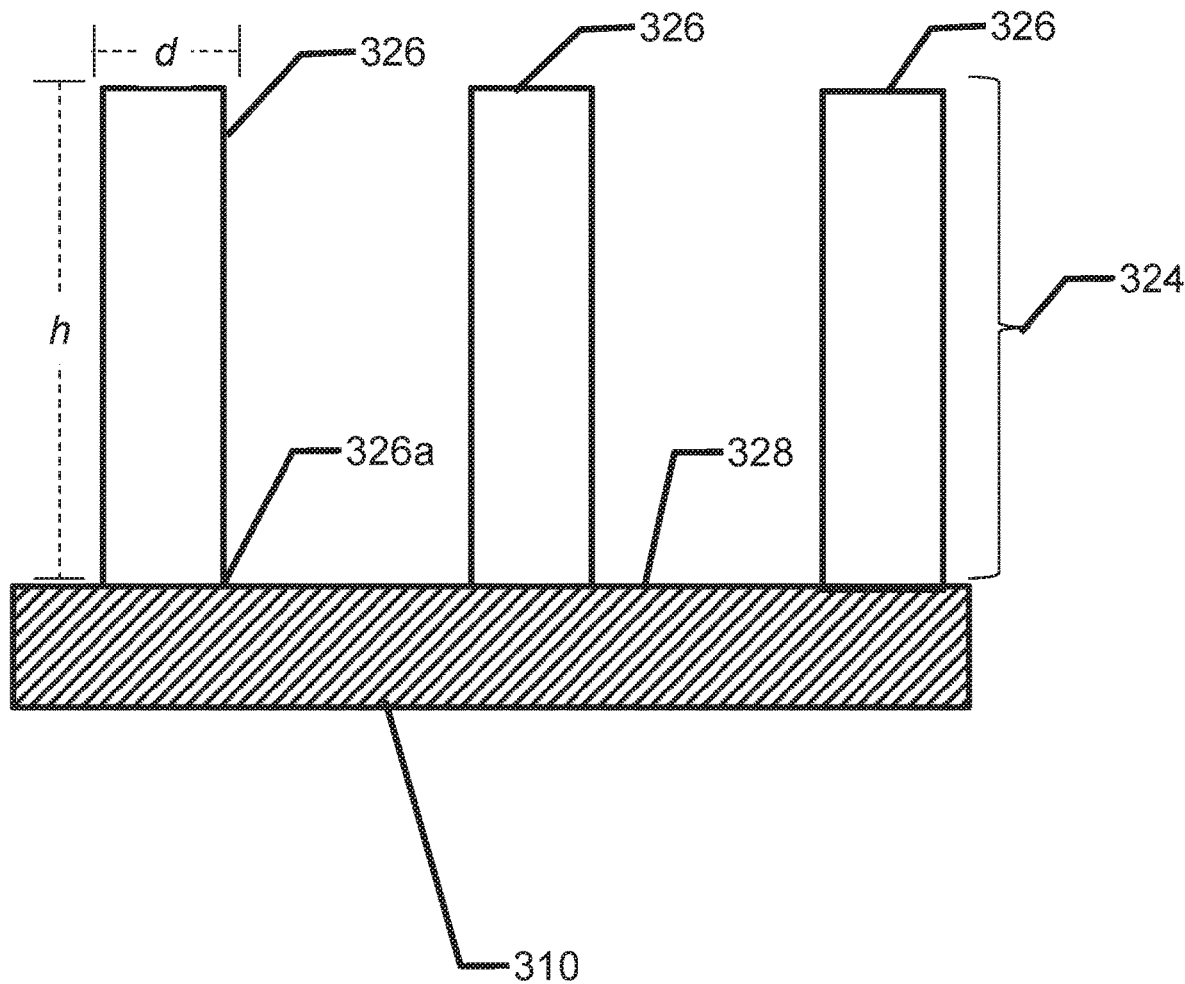
FIG. 3 is a side cross-sectional view of an expandable member according to the present disclosure.

The expandable member 110 can expand to fill at least portion of the void volume, and optionally, expand to contact the device 122 in the basin 104. Depending on the treatment system and device 122 to be treated, contact with the device 122 can be limited and, in some examples, prevented. The expandable member 110 can comprise an irregular surface to limit the amount of surface area of the device 122 engaged with the expandable member 110. The irregular surface can enable efficient exposure of the surface area of the device 122 to treatment agent. The irregular surface can comprise at least one of a texture and protrusions as illustrated in FIG. 3 below.

The expandable member 110 can comprise at least one of a balloon, a tube, a membrane, a bladder, a mechanical member, and a heater. The expandable member 110 can comprise various materials suitable for use with treatment processes. For example, the expandable member 110 can comprise a polymer, such as, for example, an elastomer. In various examples, the expandable member 110 can comprise silicone. The shape of the expandable member 110 can be any shape suitable to reduce the void volume in the basin 104 and receive the device 122. The shape of the expandable member 110 can be structured to conform to a shape of the device 122 such as an endoscope. For example, the expandable member 110 can be configured to form a cavity with a shape substantially similar to and capable of receiving the shape of the device 112.

The expandable member 110 can be configured to thermally insulate the treatment agent in the basin 104 from an environment outside of the basin 104. The thermal insulation can lessen heat losses from the treatment agent and reduce energy required to heat the treatment agent.

As illustrated in FIG. 2, a basin 204 may be provided with a plurality of expandable members 210a, 210b, 210c, and 210d to accommodate devices and basins of different sizes and configurations. An endoscope 222 can be disposed in the basin 204. Because the endoscope 222 can comprise a variety of different configurations and sizes the expandable members 210a-d can selectively move, expand, and/or contract to accommodate the different configurations and sizes of the endoscope 222 while adjusting the void volume in the basin 204. These adjustments may be performed to accommodate different size and orientations of the device 122, and/or to minimize the void volume of the basin 104 so that the amount of treatment agent can be minimized. For example, the expandable members 210a-d can move, expand, and/or contract concomitantly or independently. For example, all of the expandable members 210a-d can expand from a first state to a second state to reduce the void volume in the basin 204. For example, expandable members 210a-b can be expanded from a first state to a second state, expandable member 210c can be expanded to a third state, and expandable member 210d may be stationary and not expanded at all. In another example, one or more expandable members 110a-d may expand while other members may contract or remain stationary. Accordingly, the expandable members 210a-d can move, expand, and/or contract to adjust the void volume of the basin 104 in a variety of different manners or combinations, and the examples provided herein should not be considered limiting.

The expansion and/or contraction of the expandable members 210a-d to adjust the void volume in the basin 104 can be based on a manual adjustment or an automated adjustment. For example, an operator can manually adjust the expandable members 210a-d by changing the fluid pressure within their respective cavities utilizing the fluid source (e.g., fluid source 118 in FIG. 1). In addition, the expandable members 210a-d may be automatically adjusted to accommodate the endoscope 222. For example, a treatment apparatus comprising the basin 204 can receive an input, such as, for example, a manual input into a keypad (e.g., a serial number, a model number, a code) or a received input from another device (e.g., Radio Frequency Identification (RFID) tag). Based on the input, the treatment apparatus can automatically adjust the expandable members 210a-d via a fluid source. For example, in response to a first input the treatment apparatus may automatically adjust the expandable members 210a and 210c to a first pressure, the expandable member 210b to a second pressure, and the expandable member 210d to a third pressure.

FIG. 3 illustrates a surface 328 of an expandable member 310 comprising one example of an irregular surface 324. The irregular surface 324 of the expandable member 310 can be at least partly formed, for example, by a plurality of protrusions 326 that extend from a base surface 328 of the expandable member 310 and can be spaced apart from each other a select distance. The protrusions 326 can extend from the base surface 328 an average distance, h, of at least 1 mm as measured from their base 326a, such as, for example, at least 5 mm, at least 10 mm, or at least 20 mm as measured from their base 326a. The protrusions 326 can extend from the base surface 328 an average distance, h, of up to than 50 mm as measured from their base 326a, such as, for example, up to 20 mm, up to 10 mm, or up to 5 mm as measured from their base 326a. The protrusions 326 can extend from the base surface 328 an average distance, h, in a range of 1 mm to 50 mm as measured from their base 326a, such as, for example, 5 mm to 20 mm or 1 mm to 10 mm as measured from their base 326a.

The protrusions 326 can comprise an average diameter, d, of at least 0.1 mm such as, for example, at least 1 mm or at least 2 mm. The protrusions 326 can comprise an average diameter, d, of up to 5 mm such as, for example, up to 2 mm or up to 1 mm. The protrusions 326 can comprise an average diameter, d, in a range of 0.1 mm to 5 mm, such as, for example, 1 mm to 5 mm or 0.1 mm to 2 mm.

Referring again to FIGS. 1 and 2, a method of adjusting a void volume in the basin 104 of the treatment apparatus 100 is also provided. A device 122, such as endoscope 222, can be introduced into the basin 104 of the treatment apparatus 100. The basin 104 can comprise a void volume suitable to receive the device 122 and a treatment agent. The void volume can be adjusted to an adjusted void volume by at least one of expanding and contracting the expandable member 110 positioned in the basin 104. Expanding the expandable member 110 can comprise filling a cavity of the expandable member 110 with a fluid. Contracting the expandable member 110 can comprise removing the fluid from the cavity of the expandable member 110.

The basin 104 can be filled with the treatment agent to a volume up to the adjusted void volume. The treatment agent can be heated to a temperature in a range of 30° C. to 80° C. The device 122 can be treated with the treatment agent to at least one of clean, disinfect, and sterilize the device 122. The device 122 can be removed from the basin 104 after treating the device 122 and, optionally, by contracting the expandable member 110.

Various aspects of the invention according to the present disclosure include, but are not limited to, the aspects listed in the following numbered clauses.

1. A treatment apparatus comprising:
   a basin; and
   an expandable member disposed in the basin and configured to expand from a first state to a second state, wherein a void volume of the basin when the expandable member is in the second state is less than the void volume of the basin when the expandable member is in the first state.
2. The treatment apparatus of clause 1, wherein the expandable member comprises a cavity therein and the expandable member is configured to expand from the first state to the second state responsive to an expansive pressure within the cavity.
3. The treatment apparatus of clause 2, wherein the expandable member comprises at least one of a balloon, a tube, a membrane, a bladder, a mechanical member, and a heater.
4. The treatment apparatus of any one of clauses 2-3, further comprising a fluid source in fluid communication with the cavity, the fluid source being suitable to control a fluid pressure in the cavity.
5. The treatment apparatus of clause 4, wherein the fluid source comprises at least one of a pump and a compressed gas cylinder.
6. The treatment apparatus of any one of clauses 1-5, wherein the expandable member is formed of an elastomer.
7. The treatment apparatus of any one of clauses 1-6, further comprising a heater.
8. The treatment apparatus of clause 7, wherein the heater is suitable to heat a treatment agent to a temperature in a range of 30° C. to 80° C.
9. The treatment apparatus of any one of clauses 1-8, wherein the expandable member is operatively coupled to the basin.
10. The treatment apparatus of any one of clauses 1-9, wherein the treatment apparatus is an endoscope re-processor.
11. The treatment apparatus of any one of clauses 1-10, wherein the basin is configured to receive an endoscope.
12. The treatment apparatus of any one of clauses 1-11, wherein the expandable member further comprises an irregular surface.
13. The treatment apparatus of clause 12, wherein the irregular surface is at least partly formed by a plurality of protrusions.
14. The treatment apparatus of clause 13, wherein the protrusions extend from the surface an average distance in a range of 1 mm to 50 mm as measured from their base.
15. The treatment apparatus of any one of clauses 13-14, wherein the protrusions comprise an average diameter in a range of 0.1 mm to 5 mm.
16. A treatment apparatus comprising:
   a basin; and
   an expandable member having a cavity therein, the expandable member disposed in the basin and configured to expand from a first state to a second state responsive to an expansive pressure within the cavity, wherein a void volume of the basin when the expandable member is in the second state is less than the void volume of the basin when the expandable member is in the first state.
17. A method of adjusting a void volume in a basin of a treatment apparatus, the method comprising:
   introducing a device into the basin of the treatment apparatus, the basin comprising the void volume which is suitable to receive the device and a treatment agent; and
   adjusting the void volume to an adjusted void volume by at least one of expanding and contracting an expandable member positioned in the basin.
18. The method of clause 17, further comprising treating the device with the treatment agent.
19. The method of clause 18, wherein treating the device comprises contacting the device with the treatment agent to at least one of clean, disinfect, and sterilize the device.
20. The method of any one of clauses 18-19, further comprising removing the device from the basin after treating the device by contracting the expandable member.
21. The method of any one of clauses 18-20, further comprising heating the treatment agent to a temperature in a range of 30° C. to 80° C.
22. The method of any one of clauses 17-21, further comprising filling the basin with the treatment agent to a volume up to the adjusted void volume.
23. The method of any one of clauses 17-22, wherein expanding the expandable member comprises filling a cavity of the expandable member with a fluid, and contracting the expandable member comprises removing the fluid from the cavity of the expandable member.
24. The method of any one of clauses 17-23, wherein the treatment apparatus is an endoscope re-processor.
25. The method of any one of clauses 17-24, wherein the device is an endoscope.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

One skilled in the art will recognize that the herein described components, devices, operations/actions, and objects, and the discussion accompanying them, are used as examples for the sake of conceptual clarity and that various configuration modifications are contemplated. Consequently, as used herein, the specific examples set forth and the accompanying discussion are intended to be representative of their more general classes. In general, use of any specific exemplar is intended to be representative of its class, and the non-inclusion of specific components, devices, operations/actions, and objects should not be taken as limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A method of adjusting a void volume in a basin of a treatment apparatus, the method comprising:
   introducing a device into the basin of the treatment apparatus, the basin comprising the void volume which is suitable to receive the device and a treatment agent;
   introducing a liquid treatment agent into the basin; and
   adjusting the void volume to an adjusted void volume by at least one of expanding and contracting an expandable member positioned in the basin; and
   treating the device with the liquid treatment agent, wherein treating the device comprises contacting the device with the liquid treatment agent to at least one of clean, disinfect, and sterilize the device.

2. The method of claim 1, further comprising removing the device from the basin after treating the device by contracting the expandable member.

3. The method of claim 1, further comprising heating the liquid treatment agent to a temperature in a range of 30° C. to 80° C.

4. The method of claim 1, further comprising filling the basin with the liquid treatment agent to a volume up to the adjusted void volume.

5. The method of claim 1, wherein expanding the expandable member comprises filling a cavity of the expandable member with a fluid, and contracting the expandable member comprises removing the fluid from the cavity of the expandable member.

6. The method of claim 1, wherein the treatment apparatus is an endoscope re-processor.

7. The method of claim 1, wherein the device is an endoscope.

8. The method of claim 1, wherein the liquid treatment agent comprises ortho-phthalaldehyde.

9. The method of claim 1, further comprising immersing the device in the liquid treatment agent.

10. The method of claim 1, wherein the expandable member contacts the device.

11. The method of claim 1, further comprising circulating the liquid treatment agent within the basin.

* * * * *